United States Patent [19]
Jameson et al.

[11] Patent Number: 5,473,054
[45] Date of Patent: Dec. 5, 1995

[54] IGF-1 ANALOGS

[75] Inventors: Bradford A. Jameson, Philadelphia; Renato Baserga, Ardmore, both of Pa.

[73] Assignee: Thomas Jefferson University, Philadelphia, Pa.

[21] Appl. No.: 219,878

[22] Filed: Mar. 30, 1994

Related U.S. Application Data

[63] Continuation of Ser. No. 881,524, May 8, 1992, abandoned.

[51] Int. Cl.$^6$ .............................. A61K 38/00; C07K 7/00; C07K 7/06; C07K 7/08
[52] U.S. Cl. ........................................... 530/328; 530/327
[58] Field of Search .................................... 530/327–328; 514/12

[56] References Cited

U.S. PATENT DOCUMENTS

| | | | |
|---|---|---|---|
| 4,699,897 | 10/1987 | Jones et al. | 514/4 |
| 4,797,469 | 1/1989 | Diaz et al. | 530/324 |
| 4,876,242 | 10/1989 | Applebaum et al. | 514/3 |
| 5,070,075 | 12/1991 | Rotwein et al. | 514/12 |
| 5,077,276 | 12/1991 | Ballard et al. | 514/12 |
| 5,084,555 | 1/1992 | Coy et al. | 530/328 |
| 5,093,317 | 3/1992 | Lewis et al. | 514/12 |

FOREIGN PATENT DOCUMENTS

| | | |
|---|---|---|
| 379338 | 7/1990 | European Pat. Off. . |
| 8905822 | 6/1989 | WIPO . |

OTHER PUBLICATIONS

Bayne et al., "The C Region of Human Insulin–like Growth Factor (IGF) I Is Required for High Affinity Binding to the Type 1 IGF Receptor,", *J. of Biol. Chem.*, 264:11004–11008, 1988.
Bodanszky et al., *Peptide Synthesis*, John Wiley & Sons, 2d Ed., 1976.
Cascieri et al., "Mutants of Human Insulin–like Growth Factor I with Reduced Affinity for the Type 1 Insulin–like Growth Factor Receptor," *Biochemistry*, 27:3229–3233, 1988.
Cascieri et al., *Molecular and Cellular Biology of IGFs and Their Receptors*, LeRoth et al., eds., Plenum Press: London, 1990.
Cooke et al., "Solution Structure of Human Insulin–like Growth Factor 1: A Nuclear Magnetic Resonance and Restrained Molecular Dynamics Study," *Biochemistry* 30:5484–5491, 1991.
Foekens et al., "Prognostic Value of Estrogen and Progesterone Receptors Measured by Enzyme Immunoassays in Human Breast Tumor Cytosols," *Cancer Research*, 49:5823–5828, 1989.
Gammeltoft et al., "Expression of Two Types of Receptor for Insulin–like Growth Factors in Human Malignant Glioma," *Cancer Research*, 48:1233–1237, 1988.
Goldring et al., "Cytokines and Cell Growth Control," *Eucar. Gene Express*, 1:301–326, 1991.
Hartmann et al., "Heterogeneity of Insulin and Insulin–like Growth Factor–I Binding in a Human Burkitt Type ALL Cell Line during the Cell Cycle in Three Burkitt Type ALL Sublines," *Leukemia*, 2:241–244, 1988.
Hizuka et al., "Characterization of Insulin–like Growth Factor I Receptors on Human Erythroleukemia Cell Line (K–562 Cells)," *Endocrinol. Japan*, 34:81–88, 1987.
Jameson, B. A., "Modelling in peptide design," *Nature*, 341:465–466, 1989.
Jansen et al., "Sequence of cDNA encoding human insulin–like growth factor I precursor," *Nature*, 306:609–611, 1983.
Jaques et al., "Production of Insulin–like Growth Factor Binding Proteins by Small–Cell Lung Cancer Cell Lines," *Exp. Cancer Research*, 184:396–406, 1989.
Kent et al., *Synthetic Peptides in Biology and Medicine*, Alitalo et al., eds., Elsevier Science Publishers: Amsterdam, pp. 295–358, 1985.
Kozak et al., "Type I and II Insulin–like Growth Factor Receptors on Human Phytohemagglutinin–Activated T Lymphocytes," *Cellular Immunology*, 109:318–331, 1987.
Lee et al., "Characterization of Insulin, Insulin–Like Growth Factors I and II, and Growth Hormone Receptors on Human Leukemic Lymphoblasts," *J. Clin. Endocrinol. & Metabol.*, 62:28–35, 1986.
Massague et al., "The Subunit Structures of Two Distinct Receptors for Insulin–like Growth Factors I and II and Their Relationships to the Insulin Receptor," *J. of Biol. Chem.*, 257:5038–5045, 1982.
McOmie, *Protective Groups in Organic Chemistry*, Plenum Press: New York, 1973.
Merrifield, R. B., "Solid Phase Peptide Synthesis. I. The Synthesis of a Tetrapeptide," *J. Am Chem. Soc.*, 85:2149–2154, 1963.
Minuto et al., "Evidence for Autocrine Mitogenic Stimulation by Somatomedin–C/Insulin–like Growth Factor I on an Established Human Lung Cancer Cell Line," *Cancer Research*, 48:3716–3719, 1988.
Nakanishi et al., "Insulin–like Growth Factor–I Can Mediate Autocrine Proliferation of Human Small Cell Lung Cancer Cell Lines in Vitro," *J. Clin. Invest.*, 82:354–359, 1988.
Neurath et al., eds., *The Proteins*, vol. II, 3d Ed., Academic Press: New York, pp. 105–237, 1976.

(List continued on next page.)

*Primary Examiner*—Jill Warden
*Assistant Examiner*—S. G. Marshall
*Attorney, Agent, or Firm*—Woodcock Washburn Kurtz Mackiewicz & Norris

[57] ABSTRACT

Short peptides which function as analogs of IGF-1 are provided. These peptides abolish the proliferation of cells at nanogram concentrations. The peptides are non-toxic, and the inhibitor effect is reversible. The use of these peptides, because of their low toxicity and high efficiency, holds promises for treatment of a variety of human conditions, including prevention of restenosis of the coronary arteries after angioplasty, treatment of human neoplasia such as cancer of the prostate, treatment of tumors in pleural and peritoneal cavities and brain metastases, treatment of other abnormalities of cell growth in human beings, treatment of smooth muscle cell hyperplasia in asthma, treatment to promote burn and wound healing, and purging bone marrow from highly proliferating cells.

4 Claims, 8 Drawing Sheets

OTHER PUBLICATIONS

Ota et al., "TPA–induced neurite formation in a neuroblastoma cell line (SH–SY5Y) is associated with increased IGF–I receptor mRNA and binding," *Molec. Brain Res.*, 6:69–76, 1989.

Ota et al., "Insulin–like growth factor I receptors on mouse neuroblastoma cells," *Cur. J. Biochem.*, 174:521–530, 1988.

Pekonen et al., "Receptors for Epidermal Growth Factor and Insulin–like Growth Factor I and Their Relation to Steroid Receptors in Human Breast Cancer," *Cancer Research*, 48:1343–1347, 1988.

Pekonen et al., "Binding of Epidermal Growth Factor I and Insulin–like Growth–Factor I in Renal Carcinoma and Adjacent Normal Kidney Tissue," *Int. J. Cancer*, 43:1029–1033, 1989.

Pepe et. al., "Receptor Binding and Mitogenic Effects of Insulin and Insulinlike Growth Factors I and II for Human Myeloid Leukemic Cells," *J. Cell Physiol.*, 133:219–227, 1987.

Peyrat et al., "Insulin–like Growth Factor I Receptors in Human Breast Cancer and Their Relation to Estradiol and Progesterone Receptors," *Cancer Res.*, 48:6429–6433, 1988.

Rinderknecht et al., "The Amino Acid Sequence of Human Insulin–like Growth Factor I and Its Structural Homology with Proinsulin," *J. Biol. Chem.*, 253:2769–2776, 1978.

Ritvos et al., "Characterization of Functional Type I Insulin–Like Growth Factor Receptors from Human Choriocarcinoma Cells," *Endocrinology*, 122:395–401, 1988.

Rotwein et al., "Organization and Sequence of the Human Insulin–like Growth Factor I Gene," *J. Biol. Chem.*, 261:4828–4832, 1986.

Stewart et al., "Role of Insulin–like Growth Factors and the Type I Insulin–like Growth Factor Receptor in teh Estrogen–stimulated Proliferation of Human Breast Cancer Cells," *J. Biol. Chem.*, 265:21172–21178, 1990.

Stracke et al., "The Type I Insulin–like Growth Factor Receptor Is a Motility Receptor in Human Melanoma Cells," *J. Biol. Chem.*, 264:21544–21549, 1989.

Stuart et al., *Solid Phase Peptide Synthelia*, Pierce Chemical Company: Illinois, 1984.

Van Wyk et al., "Role of Somatomedin in Cellular Proliferation," *The Biology of Human Growth*, New York: Raven Press, 1981. pp. 223–239.

Werner et al., "Developmental regulation of the rat insulin–like growth factor I receptor gene," *Proc. Natl. Acad. Sci. USA*, 86:7451–7455, 1989.

Pietrzkowski et al., "Inhibition of Growth of Prostatic Cancer Cell Lines by Peptide Analogues of Insulin–like Growth Factor 1," *Cancer Research*, 53:1102–1106, 1993.

Pietrzkowski et al., "Inhibition of Cellular Proliferation by Peptide Analogues of Insulin–like Growth Factor 1," *Cancer Research*, 52:6447–6451, 1992.

Talavera et al., *J. Cancer Res.*, 50:3019–24 (1990).

IGF-1 ANALOGS

This is a continuation of application Ser. No. 07/881,524, filed May 8, 1992, now abandoned.

BACKGROUND

The interaction of Insulin-like Growth Factor -1 (IGF-1) with its own receptor (IGF-1 R) seems to play a major role in normal development and in the control of both normal and abnormal growth. In growth hormone disturbances of growth as, for instance, in acromegalics and in patients with growth hormone deficiency, clinical assessments of disease activity correlate far better with blood levels of IGF-1 than they do with growth hormone concentrations, Van Wyk et al., *The Biology of Normal Human Growth*, pp. 223–239, Raven Press, N.Y. (1981). Werner et al., *Proc. Nat. Acad. Sci. USA*, 86:7451–5 (1989) have shown that the mRNA levels for the IGF-1 R decrease steadily in all tissues during post-natal development, reaching a maximum during the perinatal stages. IGF-1 mRNA, instead, is not so tightly regulated during development as the mRNA for the IGF-1 R, and actually reaches maximum expression in the adult liver, which is the main site of production of IGF-1. Apart from these general considerations, a number of reports have appeared indicating that the interaction of IGF-1 with its own receptor may play a major role in cell growth. For instance, IGF-1 receptors are present in phytohemagglutinin activated T lymphocytes, Kozak et al., *Cell Immunol.*, 1009:318–331 (1987) and in K562 cells that are a human erythroleukemia cell line, Hizuka et al., *Endocrinol. Japon*, 34:81–88 (1987). In fact, K562 cells grow vigorously in serum free media (SFM) containing only IGF-1 or supraphysiological concentrations of insulin. An abundance of IGF-1 receptors has also been reported in lymphoblasts of human T cell leukemias, Lee et al., *J. Clin. Endocrinol. & Metabol.*, 62:28–35 (1986), and in HL60 cells, Pepe et al., *J. Cell Physiol.*, 133:219–227 (1987). In our own laboratory, we have been able to show that the mRNA for the IGF-1 receptor is over-expressed in HL60 cells. Again, HL60 cells, as well as other cell lines, grow well in serum-free medium containing only insulin in supraphysiological concentrations. In Burkitt cells, the number of IGF-1 receptors increase between $G_1$ and S-3 phase, Hartman et al., *Leukemia*, 2:241–4 (1988). Stem cells and progenitor cells also seem to require IGF-1 for growth. Goldring and Goldring, *Eucar. Gene Express*, 1:–301–326 (1991), list several references indicating that IGF-1 increases the proliferation of keratinocytes, smooth muscle cells, osteoblasts, chrondrocyts and neuronal cells (see their Table 4). The IGF-1 R is induced by estrogens in breast cancer cell lines, Stewart et al., *J. Biol. Chem.*, 265:21172–8 (1990), Pekonen et al., *Cancer Res.*, 48:1343–7 (1988), Peyrat et al., *Cancer Res.*, 48:6429–33 (1988), Foekens et al., *Cancer Res.*, 49:5823–8 (1989), and the expression of IGF-1 receptors seems to correlate with the growth of breast cancer, at least just as well as the estrogen receptors or the EGF receptor. Other tumors in which an increased expression of IGF-1 R or, at least, IGF-1 binding sites, have been reported include small cell lung cancer, Kiefer et al., *Exp. Cell Res.*, 184:396–406 (1989), Minuto et al., *Cancer Res.*, 48:3716–9 (1988), Nakanishi et al., *J. Clin. Invest.*, 82:354–9 (1988), choriocarcinoma cells, Ritvos et al., *Endocrinology*, 122:395–401 (1988), malignant glioma, Gammeltoft et al., *Cancer Res.*, 48:1233–7 (1988), renal carcinoma, Pekonen et al., *Int. J. Cancer*, 43:1029–33 (1989), and neoplastic human endometrium, Talavera et al., *J. Cancer Res.*, 50:3019–24 (1990). A role of the IGF-1 R in growth has also been reported in human melanoma cells, Stracke et al., *J. Biol. Chem.*, 264:21544–9 (1989), and in tumors of neural origins like neuroblastomas or pheochromocytomas, Ota et al., *Molec. Brain Res.*, 6:69–76 (1989) and Ota et al., *Cur. J. Biochem.*, 174:521–30 (1988). However, the best evidence that the IGF-1 R plays a major role in the control of cellular proliferation comes from studies with fibroblasts in cell cultures.

The 70 amino acids that comprise the human IGF-1 have been divided into 4 principle domains. The first 29 residues of IGF-1 bear a strong resemblance to the B chain of insulin and, consequently, are known as the B domain. IGF-1 residues 42–62 are homologous to the insulin A chain and hence, known as the A domain. Intervening between the B and A domains (residues 30–41) is the C domain. Finally, the last 7 amino acids (residues 63–70) have been referred to as the D domain. The sequence of IGF-1 is known (SEQ ID NO: 1). Rotwein, P., Pollock, K. M., Didier, D. K., and Krivi, C. C., *J. Biol. Chem.* 261:4828–4832 (1986) (Sequence translated from the DNA sequence); Jansen, M., van Schaik, F. M. A., Ricker, A. T., Bullock, B., Woods, D. E., Gabbay, K. H., Nussbaum, A. L., Sussenbach, J. S., and Van den Brande, J. L., *Nature* 306:609–611 (1983) (Sequence translated from the mRNA sequence); Met-24 is proposed as a likely initiator. Rinderknecht, E., and Humbel, R. E., *J. Biol. Chem.* 253:2769–2776 (1978) (Sequence of residues 49–118).

A detailed solution NMR structure of the core of human IGF-1 was recently reported by Cooke, R. M., Harvey, T. S., Campbell, I. D., *Biochem.*, 30:5484–5491 (1991). The hydrophobic core of IGF-1 is strikingly similar to insulin. In this light, it is interesting to note that, in addition to binding its own type 1 receptor, IGF-1 also binds the insulin receptor, albeit with lower affinity (Massague, J. and Czech, M. P., *J. Biol. Chem.*, 257:5038–5045 (1982)). The most striking structural differences occur between IGF-1 and an insulin dimer because of the inclusion of the C and D domains in the IGF-1 structure. Both the C and D domains were poorly resolved in the structures due to their intrinsic mobility. A molecular model of the human IGF-1 (for general details regarding the building of this molecular model see, Jameson, B. A., *Nature*, 341:465–466 (1989) that is consistent with the NMR data obtained by Cooke et al. (1991) (supra) has been developed. In this model, the C and D domains appear as "flaps" which flank the insulin-conserved receptor binding cleft (residues 21–24, Cascieri, M. A., Chicchi, G. G., Applebaum, J., Hayes, N. Green, B. C., Bayne, M. L., *Biochem.*, 27:3229–3233 (1988); Bayne, M. L., Applebaum, J., Underwood, D., Chicchi, G. G., Green, B. C., Hayes, N., Cascieri, M. A., *J. Biol. Chem.*, 264:11004–11008 (1989). It is believed that these flaps are directly involved in the specific binding to the type 1 receptor. Consistent with this notion, it has been observed that deletion of the D domain of IGF-1 increased the affinity of the mutant IGF-1 for binding to the insulin receptor, while decreasing its affinity for the type 1 receptor (Cascieri et al., 1988) (supra). Furthermore, some or all of the residues within the C domain, which flank the conserved binding cleft in IGF-1 but not in insulin, appear to be required for distinguishing between the type 1 and insulin receptors (Bayne et al., (1989) (supra); Cascieri, M. A. and Bayne, M. L., *Molecular and Cellular Biology of IGFs and Their Receptors*, LeRoth, D. and Raizada, M. K., Eds., Plenum Press (London 1990).

SUMMARY OF INVENTION

We provide direct evidence that the C and D "flaps" of IGF-1 are involved with the highly specific binding of this protein to the type 1 receptor. Targeting the C and D domains of IGF-1 for synthetic analog design has yielded highly specific competitive inhibitors of IGF-1 type 1 receptor binding. In particular, the C domain (residues 30–41) and D domain (residues 63–70) have been selected for peptide mimicry.

Synthetic peptides of less than 25 amino acids are provided comprising an amino acid sequence corresponding to the C or D domain of the human insulin-like growth factor 1. The peptide has a restricted conformation and the ability to inhibit the binding of natural IGF-1 to its cognate receptor, thereby inhibiting the action of the IGF-1 receptor.

DETAILED DESCRIPTION OF INVENTION

Synthetic peptides of less than 25 amino acids are provided which are capable of inhibiting cell proliferation. Initial synthetic analogs were designed to incorporate the amino acid sequence of the C and D domains of IGF-1. An attempt was made to maintain the distance geometries and torsional properties of the initial dihedral angles of the domains as they "bud-off" of the hydrophobic protein core. Experimental evidence as well as our theoretical calculations indicate strong conformational flexibility of these domains. In order to maximize the overlap between the conformational repertoire of the native protein with that of the synthetic analogs, we have cyclized the peptides via an artificially introduced disulfide bridge. With these restraints, the rest of the amino acid sequence of the domain should adopt a folding pattern similar to that imparted by the native structure.

The first peptide synthesized represents the looped-out region of the D domain, residues 61–69:

Native Sequence: (SEQ ID NO: 2)

Met Ala Pro Leu Lys Pro Ala Lys Ser Ala

Synthesized: (SEQ ID NO: 3)

Cys Tyr Ala Ala Pro Leu Lys Pro Ala Lys Ser Cys    [JB1].

The distance from Met-60 to Ala-70 spans ~6.0 Å, as measured in our molecular model. This distance and geometry can be maintained by the use of a disulfide bridge. The Cysteine at position 62 was replaced with an alanine in order to avoid an inappropriate disulfide linkage. The peptide was synthesized using L-amino acids and standard solid phase peptide synthesis. It should be noted that the analog described above, although a potent antagonist of the IGF-1 receptor activity, suffers from rapid degradation in sera.

In another embodiment, the L-amino acids of the peptide outlined above were substituted with D-amino acids. Because most enzymes involved in degradation recognize a tetrahedral alpha-carbon, the D-amino acids were utilized in order to avoid enzyme recognition and subsequent cleavage. Our computer studies indicate that the same folded presentation of the peptide is accomplished by reversing the amino acid sequence, employing D-amino acids. The following D-amino acid peptide was synthesized using standard solid phase techniques:

Synthesized: (SEQ ID NO: 4)

Cys Ser Lys Ala Pro Lys Leu Pro Ala Ala Tyr Cys    [JB3]

The peptides of the present invention may be prepared by any of the following known techniques. Conveniently, the peptides may be prepared using the solid-phase synthetic technique initially described by Merrifield, in *J. Am. Chem. Soc.*, 15:2149–2154 (1963). Other peptide synthesis techniques may be found, for example, in M. Bodanszky et al., *Peptide Synthesis*, John Wiley & Sons, 2d Ed. (1976); Kent and Clark-Lewis in *Synthetic Peptides in Biology and Medicine*, p. 295– 358, eds. Alitalo, K., Partanen, P. and Vakeri, A., Elsevier Science Publishers, (Amsterdam, 1985); as well as other reference works known to those skilled in the art. A summary of peptide synthesis techniques may be found in J. Stuart and J. D. Young, *Solid Phase Peptide Synthelia*, Pierce Chemical Company, Rockford, Ill. (1984). The synthesis of peptides by solution methods may also be used, as described in *The Proteins*, Vol. II, 3d Ed., p. 105–237, Neurath, H. et al., Eds., Academic Press, New York, N.Y. (1976). Appropriate protective groups for use in such syntheses will be found in the above texts, as well as in J. F. W. McOmie, *Protective Groups in Organic Chemistry*, Plenum Press, New York, N.Y. (1973). Of course, the present peptides may also be prepared by recombinant DNA techniques, although such methods are not preferred because of the need for purification and subsequent chemical modifications to conformationally restrain the peptides.

In general, these synthetic methods involve the sequential addition of one or more amino acid residues or suitable protected amino acid residues to a growing peptide chain. Normally, either the amino or carboxyl group of the first amino acid residue is protected by a suitable, selectively-removable protecting group. A different, selectively removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

In yet another embodiment, the distance from Ala-62 to Ala-70 spans ~7.5 Å. This distance and geometry can be maintained by the use of a tBoc/fMoc protection strategy to mediate the formation of an amide bond between the amino and carbon termini of the peptide. The peptide will be internally cross-linked via the side chains of a lysine (epsilon amino group) and the carboxylic acid function of an aspartic acid side chain, thus creating an amide bond. Consequently, Ala-62 and Ala-70 will be replaced with Asp and Lys, respectively. The peptide is synthesized according to standard procedures on a low substitution (0.2 mM/gm or less) paramethylbenzhydrylamine resin. The first residue added to the resin is an N-alpha-tBOC, epsilon-fMOC lysine. The rest of the peptide is continued normally using tBOC chemistry until the final residue is added. The last residue to be added is a Z-protected glutamic acid, in which the carboxylic acid moiety is protected with a tert-butyl group. Treatment of the peptide-resin with piperidine/DMF removes the fMOC group from the epsilon amino group of the initial lysine without affecting any other protection groups, and subsequent treatment with TFA removes the protection of the carboxylic acid group of the aspartic acid. Following neutralization, the peptide is covalently closed using a standard diimide-mediated coupling reaction. It should be emphasized that this is only one of the ways in which the synthetic peptide can be covalently closed, however, this method will give a flexible connection at the ends of the peptide that spans a distance of ~7.5 A from the alpha carbon of the Asp to the alpha carbon of the Lys.

Another peptide represents the looped-out region of the C domain, residues 29–38: Thr Gly Tyr Gly Ser Ser Ser Arg Arg (SEQ ID NO: 5). In order to maintain flexibility, torsional properties and distance, a Cys-Gly was placed on the amino terminus of the peptide and a Cys(D) was placed on the carboxy terminus.

In yet another embodiment, a small piece of the insulin-like core was included in this sequence in order to maintain the correct geometry. The distance spanned here represents ~10 Å. Because this is a fixed planar geometry, a toluene-based derivative will be employed to mimic the spatial properties of the native protein. An fMoc/tBoc strategy will be used to create a planar, covalent closure of the peptide between free amino groups at the ends of the peptide utilizing toluene 2,4 diisocyanate (TDI), a hetero-bifunctional cross-linker. The methyl group of the aromatic ring of TDI prevents the isocyanate group in the 2 position from reacting at a pH 7.5 or below, whereas the isocyanate group in the para position is highly reactive. A shift in pH to greater than 9.0 will initiate a reaction with the isocyanate group in the 2 position, thus enabling highly specific and controlled conditions for a 10 Å covalent closure of the peptide.

Using the amino acid sequence of IGF-1, and the molecular modelling described above, we have synthesized short peptides which function as analogs of IGF-1. The effects of treatment with these peptides are shown in FIGS. 2–8. A peptide that was synthesized to comprise the last 12 amino acids of the IGF-1 sequence, when used at nanogram concentrations, completely abolishes the proliferation of a variety of cells. The peptide is non-toxic, i.e., the cells exposed to it remain viable for long periods of time. The inhibitor effect is also reversible, i.e., when the peptide is removed and growth factors are added again, the cells resume proliferation. Inhibition is close to 100%, and it should apply to all cells that require the IGF-1/IGF-1 receptor interaction for growth. These cells include the following: fibroblasts, smooth muscle cells, chondrocytes and osteoblasts, hemopoietic cells of various lineages and keratinocytes. Several of these cell types have been actually tested, and the inhibition by the IGF-1 analog is efficient (almost 100%), and reproducible. For instance, when using the IGF-1 analog, we have inhibited the growth of fibroblasts, and fibroblast-like cells, of T-lymphocytes and of epithelial cells derived from carcinoma of the prostate.

The use of these peptides, because of their low toxicity and high efficiency, holds promises for treatment of a variety of human conditions, including prevention of restenosis of the coronary arteries after angioplasty; treatment of human neoplasia (such as cancer of the prostate); treatment of tumors in pleural and peritoneal cavities and brain metastases; treatment of other abnormalities of cell growth in human beings; treatment of smooth muscle cell hyperplasia in asthma; treatment to promote burn and wound healing; and use of this approach in purging bone marrow from highly proliferating cells.

The invention is further illustrated by means of the following, non-limiting examples.

EXAMPLES

Example 1

Figure 1:
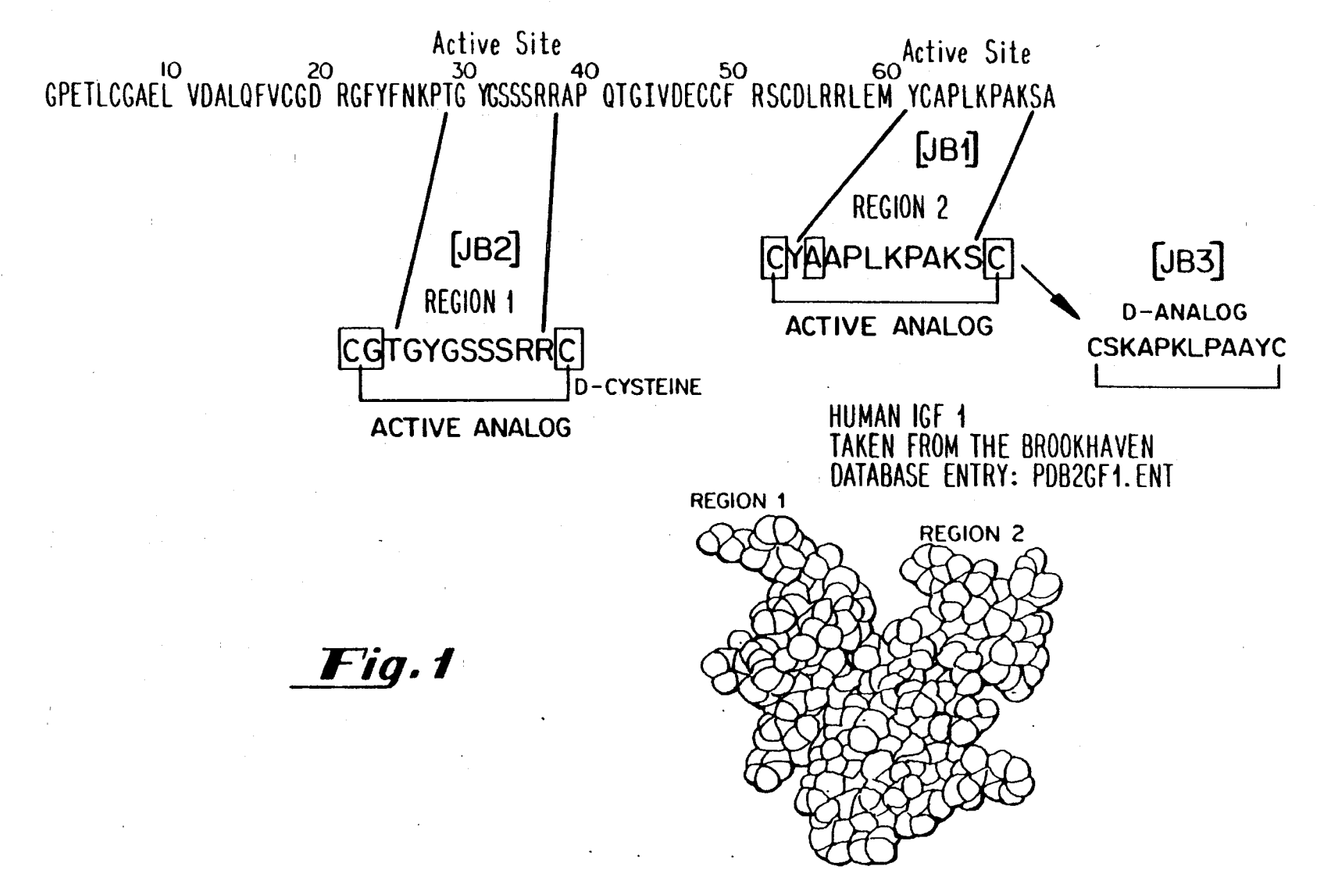
FIG. 1 shows the peptide sequences and shows the C and D "flaps" on a molecular model of the IGF-1 molecule.
Figure 2:
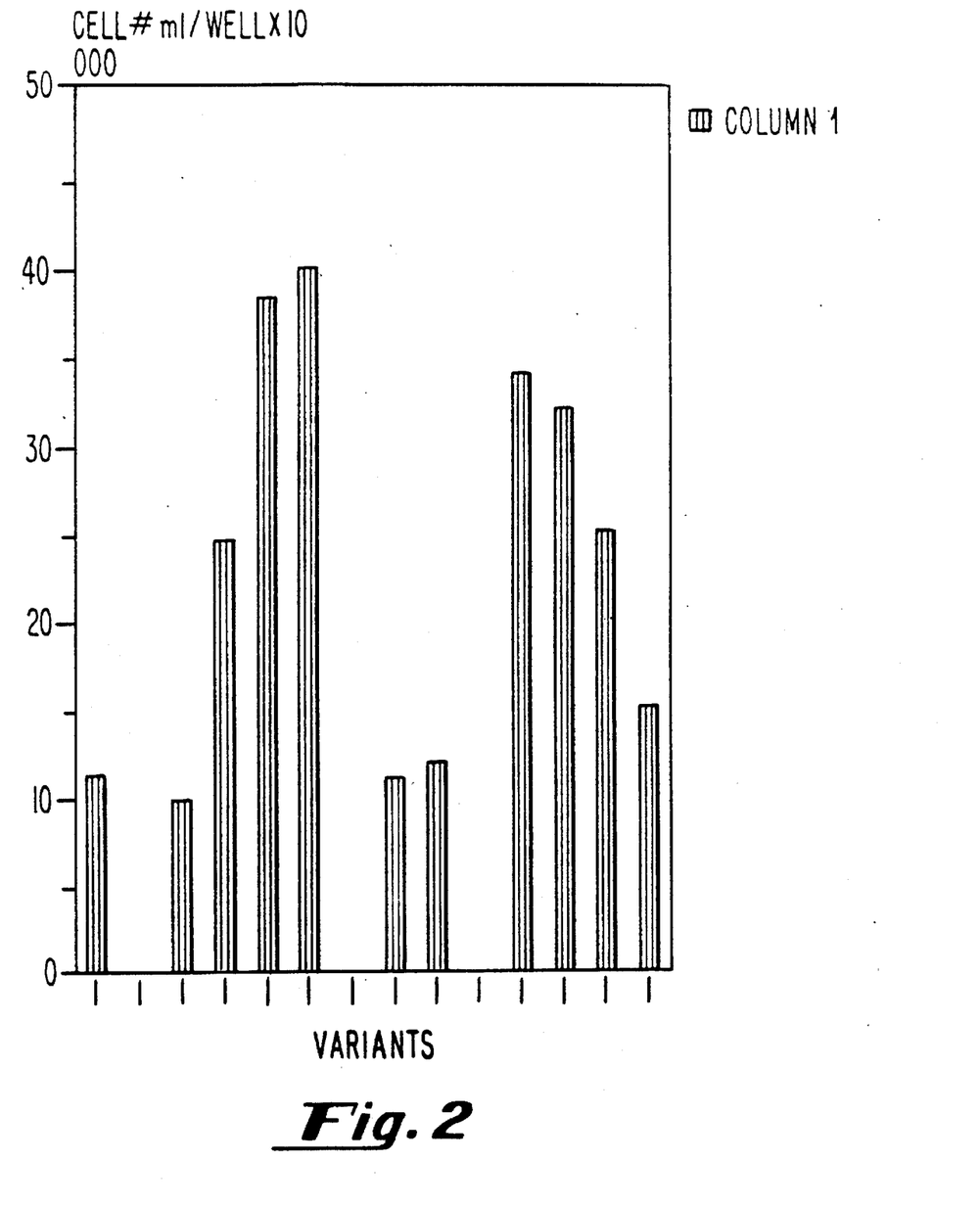
FIG. 2 shows the effect of the IGF-1 analog on the growth of p6 cells. p6 cells were cultured in SFM for 48 hours and then treated with different concentrations of JB-IGF- 1 only (bars 6, 7), or IGF-1 at a concentration of 10 ng/ml (bars 8, 11). Cells were counted 48 hours after treatment.

Effect of IGF-1 Analog on the Growth of p6 Cells p6 cells are derived from BALB/c3T3 and have a constitutively over-expressed IGF-1 receptor. Because of the constitutive over-expression of the IGF-1 receptor these cells, although incapable of growing in serum-free medium, can grow very happily when IGF-1 is added to the medium. In FIG. 2 we show the effect that the peptide had on the growth of p6 cells stimulated by IGF-1. The first bar is the number of 3T3 cells that were replated. The second bar, actually No. 3, is the number of 3T3 cells 48 hours after plating. 4, 5 and 6 represent the number of 3T3 cells 48 hours later, after stimulation with IGF-1, respectively 5 ng/ml, 10 ng/ml, 20 ng/ml. Bars 8 and 9 show the number of 3T3 cells 48 hours after exposure to the peptide analog at a concentration of 1000 ng/ml, or 100 ng/ml respectively. Note the lack of toxicity. Bars 11, 12, 13 and 14 refer to the number of 3T3 cells stimulated with 10 ng/ml of IGF-1 in the presence of the IGF-1 analog at concentrations of, respectively, 50, 100,500 and 1000 ng/ml.

Figure 3:
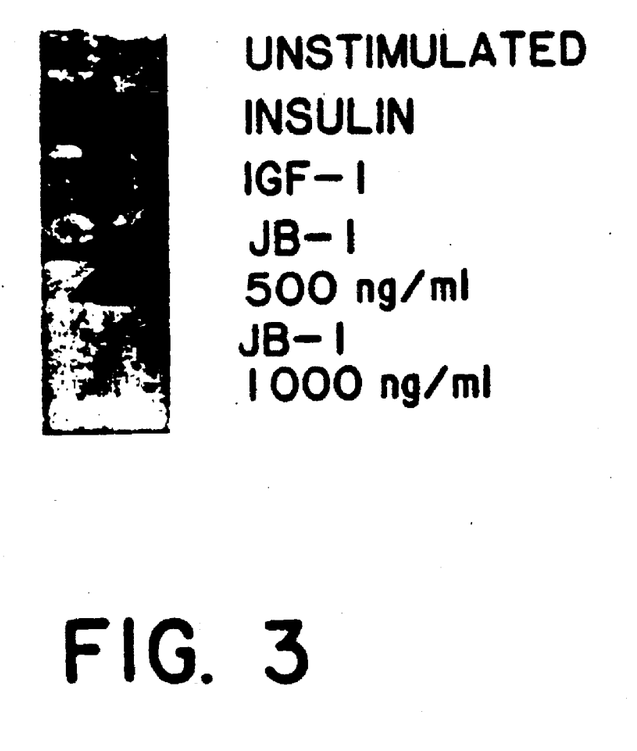
FIG. 3 shows the effect of treatment with the peptide JB1. The first band shows unstimulated cells. The second and third bands show the effects of stimulation with insulin and IGF-1, respectively. The fourth and fifth bands show the effects of treatment with JB1 at 500 ng/ml and 1000 ng/ml, respectively.

FIG. 3 shows that the analog completely inhibits the autophosphorylation of the IGF-1 receptor.

Example 2

Figure 4:
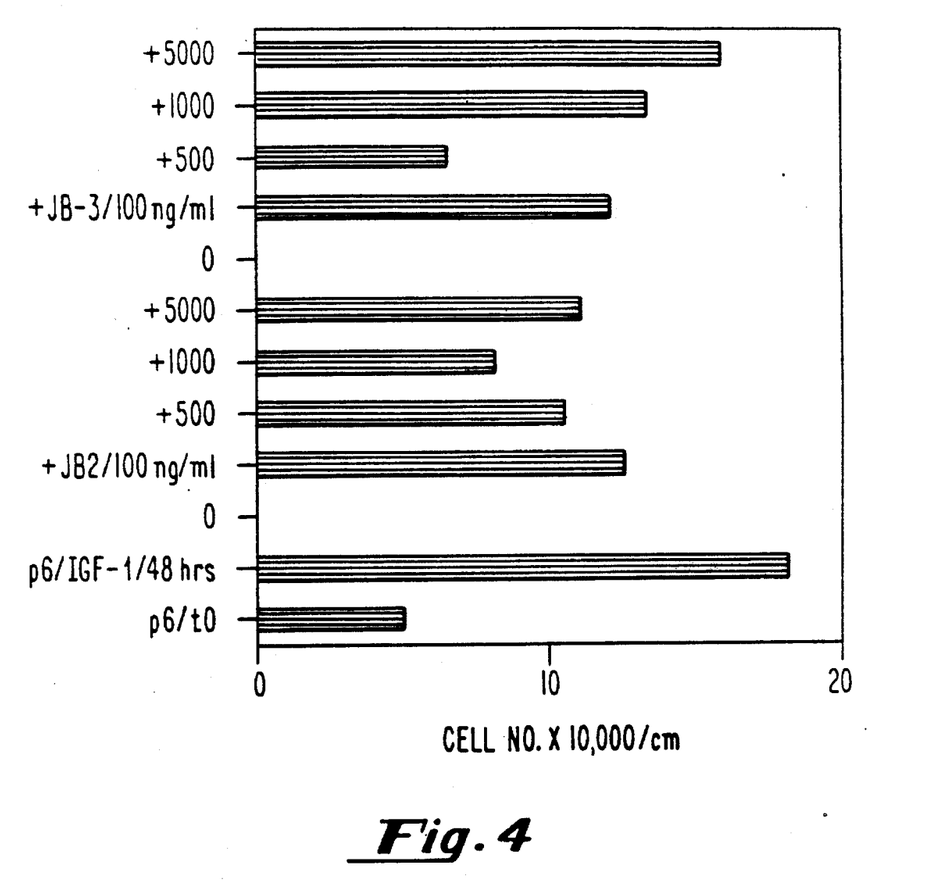
FIG. 4 shows the effect of the IGF-1 analog on the growth of p6 cells. p6 cells were treated with JB2 and JB3. The effects on growth of the cells during 48 hours in SFM after stimulation with 20 ng/ml of IGF-1 are shown.
Figure 5:
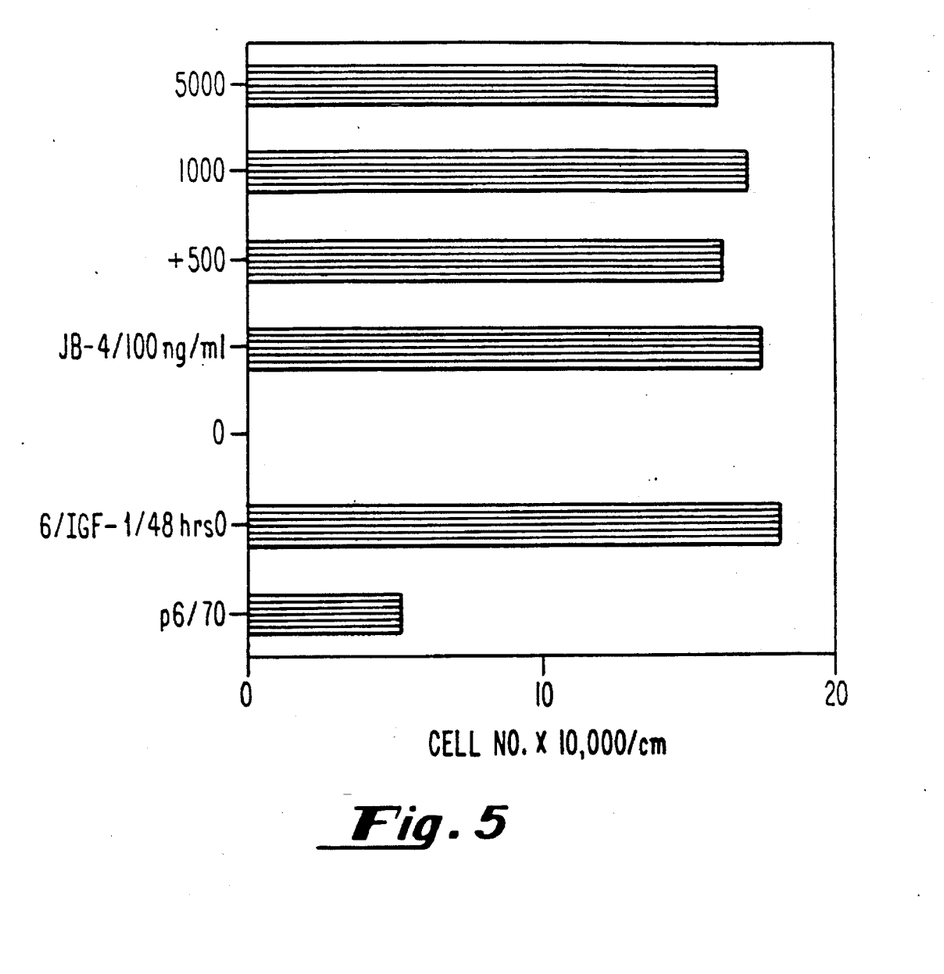
FIG. 5 shows the effects of JB4 on growth of p6 cells during 48 hours in SFM. These cells were starved in SFM for 48 hours. The peptide was added directly to conditional medium.

The experiments in Example 1 used as competitive analog the D domain peptide. FIG. 4 shows another experiment in which IGF-1-stimulated p6 cells were exposed to JB2 (C domain peptide) and JB3 (D domain peptide, but with D-amino acids). JB2 inhibits approximately 80% at 1 μg/ml, whereas JB3 completely inhibits at 500 ng/ml. The effect of a scrambled peptide (JB4, same amino acid composition as JB1 but in different order) is shown in FIG. 5. JB4 has no effect on the growth of IGF-1-stimulated p6 cells, indicating that the effect of JB1 is sequence specific.

Example 3

Figure 6:
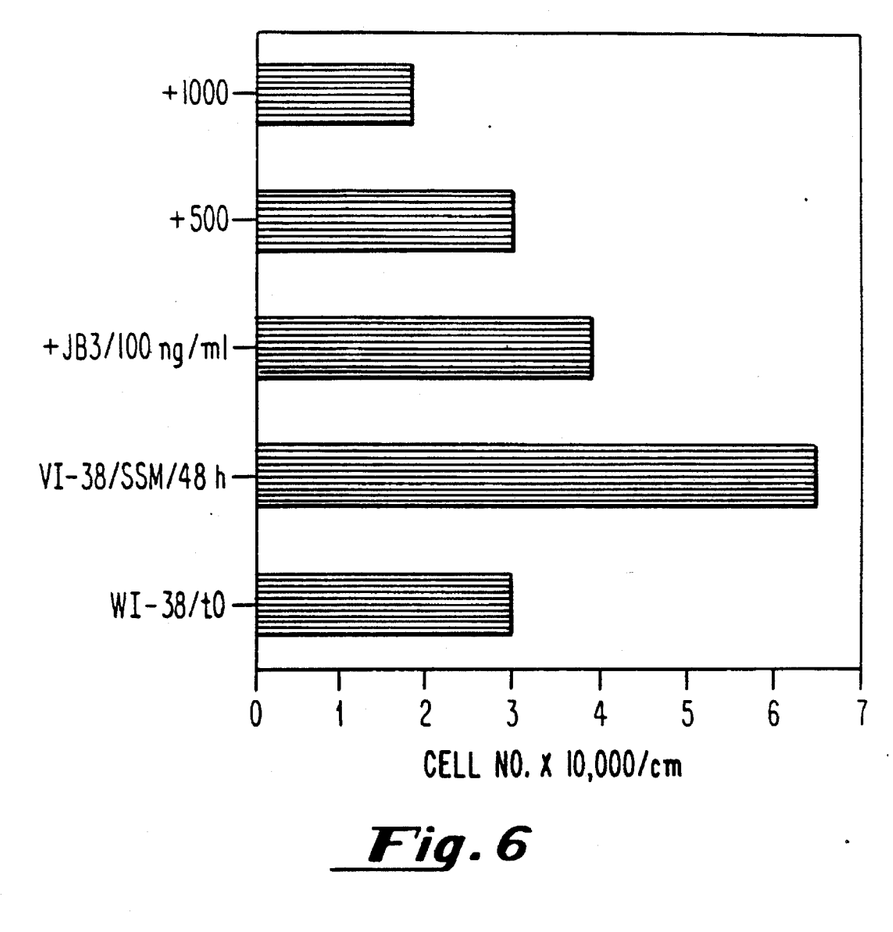
FIG. 6 shows the effects of the peptide JB3 on the growth of WI-38 cells in serum-supplemented medium (SSM) during 48 hours. Before treatment with the peptide, the cells were starved in SFM for 48 hours. After treatment, the cells were stimulated with 10% FBS.
Figure 7:
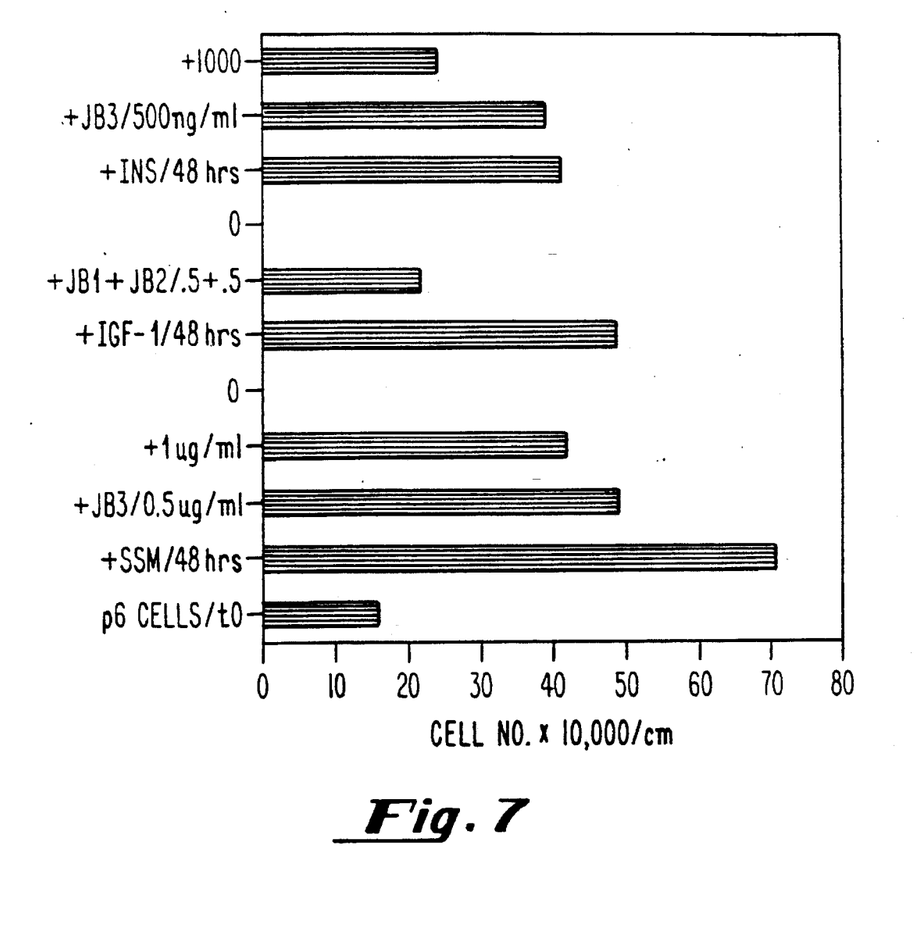
FIG. 7 shows the effects of treatment with the peptide JB3 on the growth of p6 cells in SSM with JB3 or in SFM with IGF or insulin in the presence of JB3 or JB1 and JB2 during 48 hours.
Figure 8:
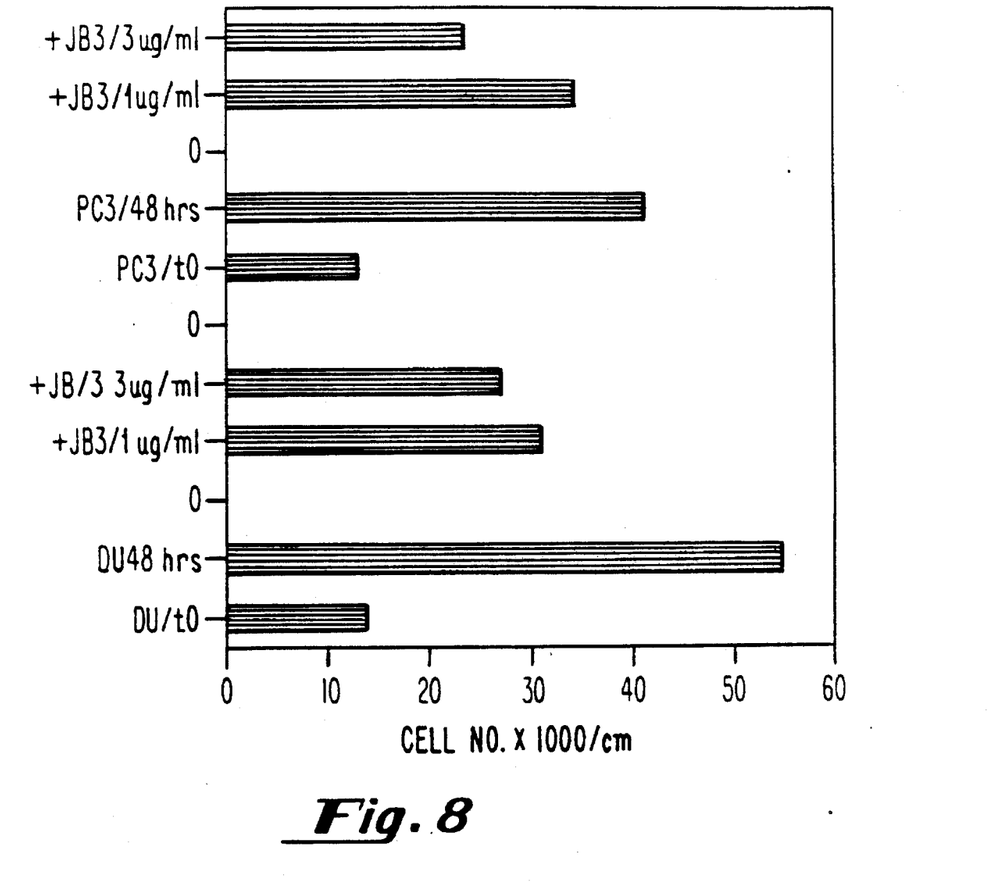
FIG. 8 shows the effect of treatment with the peptide JB3 on the growth of DU145 and PC3 cells during 48 hours in culture with serum. Cells were inoculated in SSM and 24 hours later, JB3 was added for 48 hours.

In these experiments, the inhibitory effect of JB3 (D-amino acids) was tested in serum-supplemented medium. FIG. 6 shows its effect on WI-38 human diploid fibroblasts: JB3 completely suppresses the growth of these cells at 500 ng/ml. The same results were obtained with p6 cells (FIG. 7) and with two lines of prostatic carcinoma cells, DU48 and PC3 (FIG. 8).

In summary, the following peptides have been found to exert a profound inhibitory effect on the growth of cells in culture: JB1 (D-domain peptide), JB2 (C-domain peptide) and JB3 (S-domain with D-amino acids). These peptides are nontoxic at the concentrations used (up to 5 μg/ml) and their effect is reversible. They inhibit a variety of cell types, as predicted from the finding that the activation of the IGF-1 receptor is required for the growth of many normal and transformed cells.

The inhibitory effect is sequence specific and JB3 is also active in the presence of serum.

---

What is claimed is:

1. A synthetic peptide consisting of at least 9 and less than 25 amino acids and comprising a sequence selected from the group consisting of SEQ ID NO:3, SEQ ID NO:4 and SEQ ID NO:5 wherein said peptide is a cyclic peptide and is capable of inhibiting proliferation of cells that have insulin-like growth factor 1 receptors.

2. A peptide consisting of SEQ ID NO:3.
3. A peptide consisting of SEQ ID NO:4.
4. A peptide consisting of SEQ ID NO: 5.

* * * * *

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 153
        ( B ) TYPE: amino acid
        ( D ) TOPOLOGY: linear     ( x i ) SEQUENCE DESCRIPTION: SEQ ID NO: 1:

```
Met Gly Lys Ile Ser Ser Leu Pro Thr Gln Leu Phe Lys Cys Cys
 1               5                  10                  15

Phe Cys Asp Phe Leu Lys Val Lys Met His Thr Met Ser Ser Ser
                 20                  25                  30

His Leu Phe Tyr Leu Ala Leu Cys Leu Leu Thr Phe Thr Ser Ser
                 35                  40                  45

Ala Thr Ala Gly Pro Glu Thr Leu Cys Gly Ala Glu Leu Val Asp
                 50                  55                  60

Ala Leu Gln Phe Val Cys Gly Asp Arg Gly Phe Tyr Phe Asn Lys
                 65                  70                  75

Pro Thr Gly Tyr Gly Ser Ser Ser Arg Arg Ala Pro Gln Thr Gly
                 80                  85                  90

Ile Val Asp Glu Cys Cys Phe Arg Ser Cys Asp Leu Arg Arg Leu
                 95                  100                 105

Glu Met Tyr Cys Ala Pro Leu Lys Pro Ala Lys Ser Ala Arg Ser
                 110                 115                 120

Val Arg Ala Gln Arg His Thr Asp Met Pro Lys Thr Gln Lys Glu
                 125                 130                 135

Val His Leu Lys Asn Ala Ser Arg Gly Ser Ala Gly Asn Lys Asn
                 140                 145                 150

Tyr Arg Met
        153
```

( 2 ) INFORMATION FOR SEQ ID NO: 2:

( i ) SEQUENCE CHARACTERISTICS:
        ( A ) LENGTH: 10
        ( B ) TYPE: amino acid
        ( D ) TOPOLOGY: linear -continued ( x i ) SEQUENCE DESCRIPTION: SEQ ID NO: 2:

```
Met Ala Pro Leu Lys Pro Ala Lys Ser Ala
1               5                   10
```

( 2 ) INFORMATION FOR SEQ ID NO: 3:

( i ) SEQUENCE CHARACTERISTICS:
        ( A ) LENGTH: 12
        ( B ) TYPE: amino acid
        ( D ) TOPOLOGY: linear     ( x i ) SEQUENCE DESCRIPTION: SEQ ID NO: 3:

```
Cys Tyr Ala Ala Pro Leu Lys Pro Ala Lys Ser Cys
1               5                   10
```

( 2 ) INFORMATION FOR SEQ ID NO: 4:

( i ) SEQUENCE CHARACTERISTICS:
        ( A ) LENGTH: 12
        ( B ) TYPE: amino acid
        ( D ) TOPOLOGY: linear     ( x i ) SEQUENCE DESCRIPTION: SEQ ID NO: 4:

```
Cys Ser Lys Ala Pro Lys Leu Pro Ala Ala Tyr Cys
1               5                   10
```

( 2 ) INFORMATION FOR SEQ ID NO: 5:

( i ) SEQUENCE CHARACTERISTICS:
        ( A ) LENGTH: 9
        ( B ) TYPE: amino acid
        ( D ) TOPOLOGY: linear     ( x i ) SEQUENCE DESCRIPTION: SEQ ID NO: 5:

```
Thr Gly Tyr Gly Ser Ser Ser Arg Arg
1               5
```